(12) United States Patent
Cirino

(10) Patent No.: US 10,488,837 B2
(45) Date of Patent: *Nov. 26, 2019

(54) SYSTEMS, DEVICES AND METHODS FOR CONTROLLING AND UTILIZING SMART WINDOWS

(71) Applicant: Associated Materials, LLC, Cuyahoga Falls, OH (US)

(72) Inventor: Christian Aaron Cirino, Ravenna, CA (US)

(73) Assignee: Associated Materials, LLC, Cuyahoga Falls, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/176,588

(22) Filed: Oct. 31, 2018

(65) Prior Publication Data

US 2019/0146442 A1 May 16, 2019

Related U.S. Application Data

(63) Continuation of application No. 15/815,360, filed on Nov. 16, 2017.

(51) Int. Cl.
*G05B 19/042* (2006.01)
*E06B 3/92* (2006.01)
(Continued)

(52) U.S. Cl.
CPC ............ *G05B 19/0425* (2013.01); *E06B 3/92* (2013.01); *G01N 33/0073* (2013.01);
(Continued)

(58) Field of Classification Search
CPC .......... E06B 3/92; E06B 3/6775; E06B 3/677; D01N 33/0073; G05B 15/02; H04L 12/2803; H04W 68/005; G01M 3/3272
See application file for complete search history.

(56) References Cited

U.S. PATENT DOCUMENTS 5,595,075 A 1/1997 Chen
8,350,697 B2 * 1/2013 Trundle ................ G08C 19/16
340/539.3
(Continued)

OTHER PUBLICATIONS

Wikipedia, "normalizing constant and Normalization", Jul. 14, 2019, pp. 6, downloaded from the internet https://en.wikipedia.org/wiki/Normalizing_constant (Year: 2019).*

(Continued)

*Primary Examiner* — Brian W Wathen
*Assistant Examiner* — Olvin Lopez Alvarez
(74) *Attorney, Agent, or Firm* — Knobbe, Martens, Olson & Bear LLP

(57) ABSTRACT

A window is described, comprising a frame, a sash, a window pane mounted in the sash, a computer system, the computer system comprising a housing, the housing configured to be mounted into a receiving area of the frame, into the sash, into a window valence, or into a window casing. A processing device is located within the housing. Non-transitory memory located within the housing configured to store instructions to be executed by the processing device, a network interface, at least a first sensor fixed to the casing, frame, or window pane, the first sensor coupled to the computer system, wherein the computer system is configured to take at least a first action in response to at least a first sensor reading from the first sensor.

30 Claims, 10 Drawing Sheets

(51) Int. Cl.
H04L 12/28 (2006.01)
G01N 33/00 (2006.01)
G05B 15/02 (2006.01)
H04W 68/00 (2009.01)
E06B 3/44 (2006.01)

(52) U.S. Cl.
CPC .......... *G05B 15/02* (2013.01); *H04L 12/2803* (2013.01); *H04L 12/2823* (2013.01); *H04W 68/005* (2013.01); E06B 2003/4484 (2013.01); G05B 2219/2642 (2013.01); H04L 2012/285 (2013.01)

(56) References Cited

U.S. PATENT DOCUMENTS

| | | | | |
|---|---|---|---|---|
| 8,643,933 | B2* | 2/2014 | Brown | H01R 41/00 359/275 |
| 9,157,902 | B2* | 10/2015 | Gore | G08B 13/04 |
| 9,898,912 | B1* | 2/2018 | Jordan, II | G08B 21/02 |
| 10,030,885 | B1* | 7/2018 | Yu | F24F 11/70 |
| 2002/0126009 | A1* | 9/2002 | Oyagi | G08B 25/10 340/541 |
| 2003/0149550 | A1* | 8/2003 | Famili | G05B 23/0235 702/188 |
| 2004/0217832 | A1 | 11/2004 | Lamb et al. | |
| 2005/0209710 | A1* | 9/2005 | Andersen | F24F 11/0001 700/19 |
| 2005/0237214 | A1 | 10/2005 | Sanchirico, Jr. et al. | |
| 2006/0028334 | A1* | 2/2006 | Adonailo | G08B 13/04 340/522 |
| 2006/0119476 | A1* | 6/2006 | Hope | G08B 13/1427 340/521 |
| 2006/0290561 | A1* | 12/2006 | Praskovsky | G01S 13/87 342/26 D |
| 2007/0069894 | A1 | 3/2007 | Lee et al. | |
| 2007/0085676 | A1* | 4/2007 | Lee | G08B 25/08 340/539.18 |
| 2007/0194914 | A1 | 8/2007 | Gates et al. | |
| 2007/0198850 | A1* | 8/2007 | Martin | G07C 9/00087 713/186 |
| 2008/0127566 | A1 | 6/2008 | Morton | |
| 2008/0276542 | A1 | 11/2008 | Morton | |
| 2009/0140858 | A1* | 6/2009 | Gore | G08B 13/04 340/547 |
| 2009/0161720 | A1* | 6/2009 | Pelletier | G01N 25/72 374/4 |
| 2009/0302995 | A1 | 12/2009 | Park | |
| 2011/0087370 | A1* | 4/2011 | Denison | G07C 9/00571 700/236 |
| 2011/0133940 | A1* | 6/2011 | Margalit | E06B 3/66366 340/584 |
| 2012/0215075 | A1* | 8/2012 | Surace | A61B 5/0002 600/301 |
| 2012/0268803 | A1* | 10/2012 | Greer | E06B 9/24 359/275 |
| 2013/0174488 | A1* | 7/2013 | Snider | B60J 1/1853 49/70 |
| 2014/0160550 | A1* | 6/2014 | Brown | H04L 12/2803 359/275 |
| 2014/0259931 | A1* | 9/2014 | Plummer | H05K 7/14 49/70 |
| 2014/0313028 | A1* | 10/2014 | Jiang | G08B 13/1672 340/506 |
| 2015/0130603 | A1* | 5/2015 | Lee | B60R 16/0236 340/439 |
| 2015/0180713 | A1* | 6/2015 | Stewart | H04L 41/0813 709/220 |
| 2015/0223705 | A1* | 8/2015 | Sadhu | G01S 19/17 600/301 |
| 2015/0243197 | A1 | 8/2015 | Boylan | |
| 2015/0325096 | A1* | 11/2015 | Hatch | F24F 11/30 340/601 |
| 2015/0348387 | A1* | 12/2015 | Sheflin | G08B 19/00 340/539.22 |
| 2016/0047158 | A1* | 2/2016 | Raap | E06B 3/44 49/31 |
| 2016/0062332 | A1* | 3/2016 | Call | G05B 19/042 700/276 |
| 2016/0134932 | A1* | 5/2016 | Karp | H04W 4/80 348/155 |
| 2016/0205706 | A1* | 7/2016 | Noda | H04W 76/10 455/418 |
| 2016/0323548 | A1* | 11/2016 | Khot | G06F 3/04842 |
| 2016/0343239 | A1* | 11/2016 | Lamb | G08B 25/10 |
| 2017/0002595 | A1* | 1/2017 | Keller, Jr. | E05F 15/40 |
| 2017/0123391 | A1 | 5/2017 | Sinha | |
| 2017/0124836 | A1* | 5/2017 | Chung | H04W 4/90 |
| 2017/0170776 | A1* | 6/2017 | Janowski | H02S 20/26 |
| 2017/0205105 | A1* | 7/2017 | Adam | F24F 11/30 |
| 2017/0212399 | A1* | 7/2017 | Tarng | E06B 7/10 |
| 2017/0248951 | A1* | 8/2017 | Perkins | G05D 1/0248 |
| 2017/0248953 | A1* | 8/2017 | Kelley | B62D 15/0265 |
| 2017/0285432 | A1* | 10/2017 | Shrivastava | G05B 15/02 |
| 2018/0051509 | A1* | 2/2018 | German | E06B 5/10 |
| 2018/0106092 | A1* | 4/2018 | Singh | E05F 15/73 |
| 2018/0224817 | A1* | 8/2018 | Shih | G05B 23/024 |
| 2018/0266163 | A1* | 9/2018 | Combe | E05F 15/72 |
| 2018/0284521 | A1* | 10/2018 | Kong | G02F 1/13473 |
| 2019/0108739 | A1* | 4/2019 | Wedig | G08B 21/182 |

OTHER PUBLICATIONS

Smart Home FAQ, Verilock Security Sensors, downloaded from https://www.andersenwindows.com/connect/ on Sep. 12, 2017, 4 pp.
Smart Home Solutions, Webpage at https://www.andersenwindows.com/connect/ , printed on Sep. 12, 2017, pp. 10.
Spec Sheet, Andersen® VeriLock® Wireless Security Sensors, © 2016, 3 pp.
User's Guide for E-Series/Eagle® VeriLock®, Honeywell International, Rev. Jul. 28, 2014, 15 pp.
VeriLock® User's Security Sensor User's Guide, Andersen Windows, Rev. May 10, 2016, 13 pp.

* cited by examiner

SYSTEMS, DEVICES AND METHODS FOR CONTROLLING AND UTILIZING SMART WINDOWS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present invention generally relates to sensor and control systems, and more particularly to automation systems, such as those using Internet of Things (IoT) systems, devices, and processes.

Background

The Internet of Things (IoT) may be used to inter-network electronic devices and to exchange data between and amongst such devices. The IoT enables objects to be sensed or controlled remotely over one or more networks.

SUMMARY

The following presents a simplified summary of one or more aspects in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later.

An aspect of the disclosure relates to window, comprising a frame; a sash; a window pane mounted in the sash, a computer system, the computer system comprising a housing, the housing configured to be mounted into a receiving area of the frame, into the sash, into a window valence, or into a window casing, a processing device located within the housing. Non-transitory memory located within the housing configured to store instructions to be executed by the processing device, a network interface, at least a first sensor fixed to the casing, frame, or window pane, the first sensor coupled to the computer system, wherein the computer system is configured to take at least a first action in response to at least a first sensor reading from the first sensor.

An aspect of the disclosure relates to a window, comprising: a sash; a window pane mounted in the sash; a motor configured to open and close the sash in response to a respective open command and close command; a network interface; a plurality of sensors, including a first sensor configured to measure a position of the sash, a second sensor configured to detect breakage of the window pane, and a third sensor that detects an environment condition related to air, light, and/or weather; a computer system, the computer system comprising: a processing device; non-transitory memory located configured to store instructions to be executed by the processing device, that when executed cause the computer system to perform operation comprising: receiving information from the second sensor and/or the third sensor; determining, based at least in part on the information from the second sensor and/or the third sensor, if a first set of criteria is met; in response to determining that the first set of criteria is met, commanding the motor to open or close the sash; commanding at least one device remote from the window to take a first action.

An aspect of the disclosure relates to a movable panel, such as a window or door, comprising: a network interface; a plurality of sensors, including a first sensor configured to measure a position of the panel, a second sensor configured to detect breakage of a glass pane, and a third sensor that detects an environment condition related to air, light, and/or weather; a computer system, the computer system comprising: a processing device; non-transitory memory located configured to store instructions to be executed by the processing device, that when executed cause the computer system to perform operation comprising: receiving information from the second sensor and/or the third sensor; determining, based at least in part on the information from the second sensor and/or the third sensor, if a first set of criteria is met; in response to determining that the first set of criteria is met, commanding the motor to open or close the panel; commanding at least one device remote from the panel to take a first action.

An aspect of the disclosure relates to a method, comprising: monitoring, by a computer system included in an openable barrier comprising a door and/or a window, the openable barrier comprising at least a first glass panel and a second glass panel in parallel with the first glass panel, and a noble gas between the first glass panel and the second glass panel: a first sensor configured to determine pressure information with respect to a pressure between the first glass panel and the second glass panel; and at least partly in response to pressure information from the first sensor indicating that that the pressure between the first glass panel and the second glass panel fails to meet a first criterion, transmitting an alert to one or more predefined destinations using a wireless communications interface.

An aspect of the disclosure relates to a method, comprising: monitoring, by a computer system included in an openable barrier comprising a door and/or a window, a first sensor; and at least partly in response to information from the first sensor, transmitting an alert or command to one or more predefined destinations.

Figure 1:
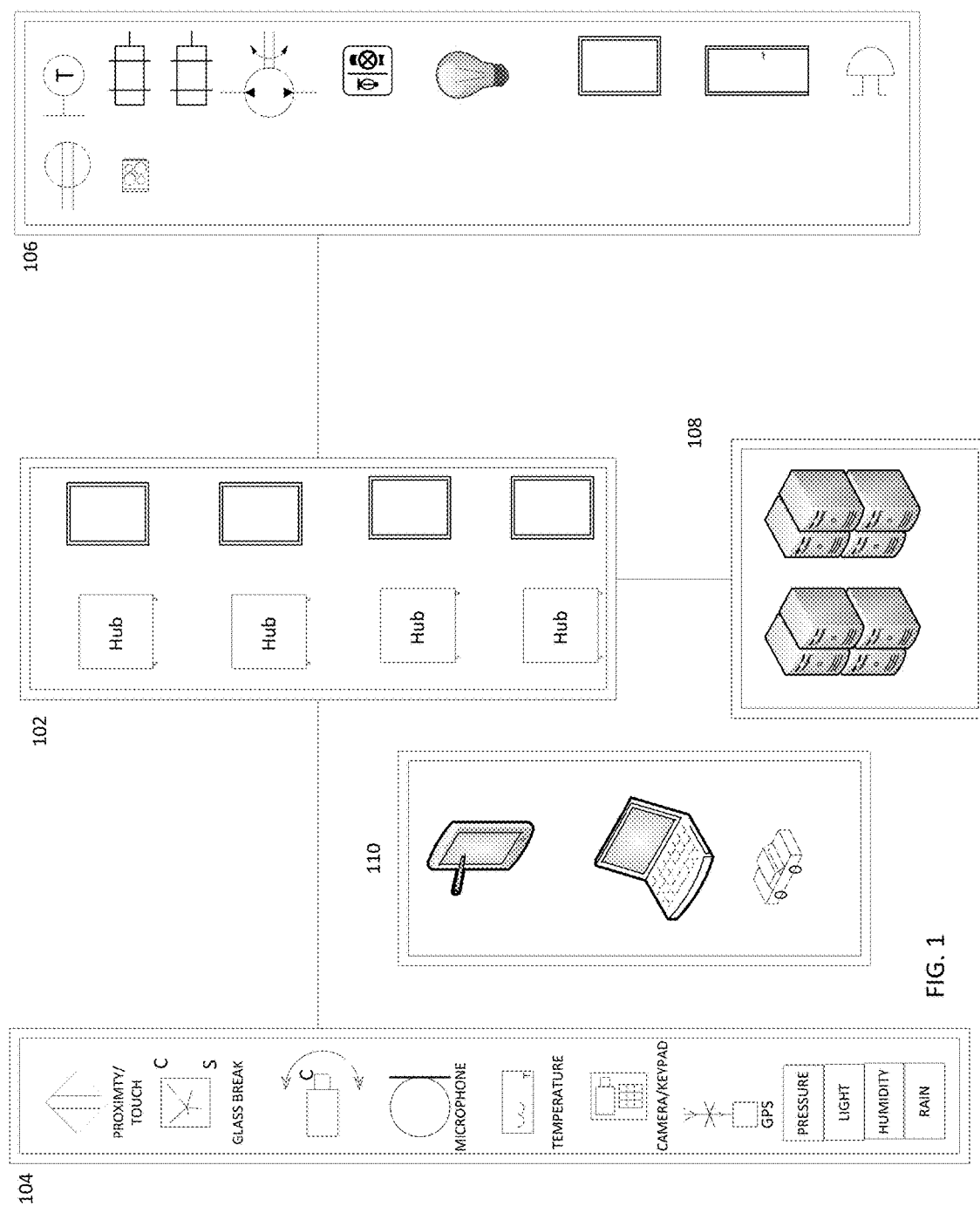
FIG. 1 illustrates an example architecture.

While each of the drawing figures illustrates a particular aspect for purposes of illustrating a clear example, other embodiments may omit, add to, reorder, and/or modify any of the elements shown in the drawing figures. For purposes of illustrating clear examples, one or more figures may be described with reference to one or more other figures, but using the particular arrangement illustrated in the one or more other figures is not required in other embodiments.

DETAILED DESCRIPTION

Methods and systems are described that utilize a computerized system to provide a variety of services. The system may optionally utilize a smart window (e.g., double hung window, single hung window, sliding window, casement window, awning window, hopper window, skylight, or the like) that includes sensors, output devices, and a local processing device. It is understood that although examples may be discussed with respect to windows, other openable barriers mounted to a structure, such as doors (e.g., patio doors, entry doors, interior doors, emergency doors, and the like) and the like may be used in such examples. By way of example, the openable barriers may be mounted to pivots (e.g., wall or ceiling mounted hinges) to allow the openable barrier to rotate to an open or closed position. By way of further example, the openable barriers may be configured to be slidably opened and closed (e.g., with one or more sides positioned within a channel). The openable barrier may include a fixed and/or openable glass portion. For example, the openable barrier may be a patio door comprising a framed glass panel, or a door with an openable window panel.

Because of window characteristics and placement, windows and/or doors may be advantageously configured as a hub of sensors to detect environmental conditions of a building, such as a house. Further, the intelligent control of windows (e.g., opening, closing, shading, etc.) and/or doors may be advantageous in conserving energy, making structures more comfortable for their inhabitants, and in preventing damage from the elements.

For example, windows are a primary entry path via which the outside environment may impinge on the interior of a building. By way of illustration, windows allow light (e.g., visible, infrared, and ultraviolet light) to enter a building providing illumination and allowing heat to enter the building via light or thermal transmission. A window is also a primary path via which heat may exit a structure. Further, an open or broken window may allow rain to enter a structure. Still further, windows flex in response to strong winds or changes in pressure, providing an indication as to weather conditions. Yet further, windows are a common point of entry for burglars.

In order to take advantageous of the characteristics of windows, a window may be optionally be configured with sensors and may optionally be configured with a modular data processing system. For example, a window system may be equipped with a computing device, a memory system, wired and/or wireless network interfaces, one or more sensors, one or more output devices, one more electro-mechanical devices, and one or more user interfaces to control or provide inputs to the window system. A door may be similarly configured.

The window system may optionally include a power supply configured to be connected to an AC and/or DC power source. The window system may optionally include a battery to provide normal operating power and/or to provide backup power in the event external power has been interrupted. The battery may optionally be rechargeable via a power source. The window system may optionally be connected to a photovoltaic power source. The window system may optionally include an integral photovoltaic system to power the window system and/or to recharge a window system battery. A door may be similarly configured.

For example, the window glass may be coated with solar cells that are substantially transparent to visible light (e.g., 60% or more) but absorb infrared and/or ultraviolet light, which is converted to electricity. Such solar cells may optionally utilize an organic solar coating rather than being inorganic, silica-based. Alternatively or in addition, very thin solar cells (e.g., one-tenth of a micrometer thick) may be mounted to the window glass that absorb some visible light (optionally in addition to infrared and/or ultraviolet light) but allow a significant amount of visible light to pass through. Still further, segmented solar cells may be mounted to the window glass.

Each electronically equipped window may be associated with a unique identifier, such as a unique IP address. Optionally, some or all of the sensors, electro-mechanical devices, output devices, other components described herein, and the like, may also be assigned a unique identifier, such as a unique IP address.

Example of sensors that may be integrated into a window or door (e.g., in a casing (e.g., decorative molding or framing around a window to cover the space between the window frame or jamb and the wall), frame, valance, sill, glass, or the like) will now be discussed. Optionally, a given sensor may be connected to the window (or door) via a wired or wireless interface, but not be integrated into the physical structure of the frame.

By way of example, the sensors may optionally include one or more of the following:

Lock sensor;
Sunlight intensity sensor (e.g., a multi-channel light sensor configured to detect UV-light, visible light and infrared light);
UV sensor;
Infrared sensor;
Visible light sensor;
Pressure sensor (e.g., to detect pressure of a noble gas between panes of glass);
Humidity sensor;
Indoor temperature sensor;
Outdoor temperature sensor;
Rain sensor;
Barometric pressure sensor;
Air quality sensor (e.g., criteria pollutant sensors, sensors to detect volatile organic compounds (VOCs), particle sensors, and/or the like);
Pollen count sensor;
Dust sensor;
Flex sensor (e.g., to detect flex in window or door panes);
Sound sensor (e.g., microphone);
Vibration sensor;
Accelerometer;
Tilt sensor;
Position sensor (e.g., window or shade open, closed, or an intermediate position);
Smoke detector;
Liquid detector;
Heat detector;
Carbon monoxide detector;
Natural gas detector;
Location sensor (e.g., GPS radio);
Direction sensor (e.g., compass);
Breakage sensor;
Motion detector (exterior);
Motion detector (interior);
Proximity detector,
Camera (interior); and/or
Camera (exterior).

By way of example, window user interface devices (which may be integrated into the physical structure of the window via one or more removable modules) may include one or more of the following:

Display (e.g., using LCD, OLED, plasma, e-ink, dot matrix, segment and/or other display technologies);
Touch screen (which may be utilized in conjunction with a display to provide a touch screen display);

Physical controls (e.g., physical buttons, switches, rotary controls, slide switches, etc.);

Touch sensitive switches (e.g., mounted into the window casing, frame, valance, sill, shade, shutter, etc.);

Discrete notification indicator (e.g., power-on/off, WiFi connected/disconnected, Bluetooth connected/disconnected, fault indication, low power, charging, and/or other indicators);

Speaker;

Siren;

Microphone (e.g., to receive voice commands);

Cameras (e.g., to detect hand/finger gestures, arm gestures, other body part gestures, facial expressions, and/or the like, where such gestures and expression may optionally be interpreted by the window computer system as corresponding to instructions);

Haptic device;

Illumination light (e.g., a floodlight, a spotlight, nightlight, an RGB light; and/or Auto-deploy safety ladder, etc.

Optionally, certain user interfaces, such as the display, touch screen, or touch sensitive switch may be mounted on the window glass. Optionally, such user interfaces may be substantially transparent so as to be difficult to see with the naked eye, but in response to detecting that a user is proximate to the window (e.g., via a proximity detector or in response to the user activating a switch), the window system may cause the user interfaces to become visible.

The window system may optionally be wirelessly or via a wired interface connected to a remote user terminal, such as a smart phone, a tablet computer, a desktop computer, a smart wearable (e.g., a smart watch), a networked microphone/speaker device, a networked television, a set top box, a dedicated wall mounted tablet or keypad, a camera, and/or the like. Thus, the user may interact with the window system via a terminal, optionally even from a remote location. For example, the user may provide input via a keyboard/keypad, touch screen, pointing device, voice, camera, or otherwise. Status and confirmation of user instructions may be received by a user device and provided visually via a user device display, haptically, and/or audibly via a user device speaker.

Example of electro-mechanical devices that may be integrated into a window (e.g., into a window crank, a window lock, a window casing/frame, a valance, a sill, or the like) will now be discussed. Optionally, a given electro-mechanical device may be connected to the window via a wired or wireless interface, but not be integrated into the physical structure of the window. By way of example, the electro-mechanical devices may optionally include one or more of the following:

Window motor (e.g., to open, close, or otherwise change position of movable window);

Shade/blind motor (e.g., to open, close, or otherwise change position of a window shade or blind);

Blind rotation motor (e.g., to rotate position of a window blind);

Camera motor (e.g., to rotate a camera to a desired position);

Light fixture motor (e.g., to rotate an illuminating lighting device to a desired position);

Electrochromic active panel;

Power outlet;

Window lock/unlock motor;

Door lock/unlock motor;

Sprinkler and/or other irrigation motor, and/or

Other motors.

Unless indicated otherwise, a motor may be an electric motor, a gas motor, a solenoid, or other motive imparting device. In addition, a window may include electro-chromatic glass, and a controller may be provided to control the color, tint, glazing, and/or transmissivity of the glass. For example, the system may control the electro-chromatic glass to reduce or increase the amount of light that is transmitted into the structure, to provide additional or reduced privacy, or to change the window glass color or an image depicted via the glass to suit a desired mood.

It is understood that given device may include both sensors and motors (e.g., a motorized camera, etc.).

The window system may wirelessly connect to other systems collocated at the same structure (e.g., the same home or other building) or located at remote structures. For example, a given smart window may connect to thermostats, alarm systems and sensors, door locks, window locks of other windows or doors, other color/tint controllers for other windows or doors, water pumps, water valves, sprinklers, gas valves, curtains, shades, blinds, appliances (e.g., coffee machines, refrigerators, ovens, etc.), medical alert devices (e.g., portable wearables such as medical alert buttons which may be worn, heart rate sensors, electrocardiographic (ECG) sensors, electromyographic (EMG) sensors, hypoglycemia sensors, fall detect sensors, respiratory sensors, etc.), and/or the like. The window may, in cooperation with other window systems having WiFi radios, establish a mesh network, wherein a given window system acts as a node in the mesh network, and may relay data from one node to another node in the network, The system may optionally wirelessly connect to vehicles to detect a given vehicle's position, determine a vehicle destination, determine a vehicle time of arrival, and/or to provide information for display or audible playback by the vehicle.

The window system may also connect via a wired and/or wireless interface to one or more remote systems. For example, the window system may connect to a remote system to download software, to transmit data collected by the window system to the remote system (e.g., regarding the window environment, regarding the window systems performance, regarding any detected window system failures, and/or the like), to receive data from the remote system, to receive commands from the remote system, to transmit commands to the remote system, and/or the like.

The window system may optionally be modular to enable existing or new modules to be added to the window system and to permit easy repair and updates. For example, the window computer system may be positioned in a housing which may be configured to be easily removed from the window (and replaced in the window) by an end user (e.g., a home owner) using readily available simple tools, such as a screw driver or a coin, or using no tools. Such modularity enables a user to easily repair or to upgrade the window system computer system with an upgraded computer system (e.g., with increased computing capability, additional memory, higher performance or more modern wireless interface, and/or the like). The window computer system may, for example, be installed in the window valance, frame, casing, or sill. Exterior wall surfaces of the housing may optionally be flush with surfaces of the window casing/frame, valance, or sill when installed so as to appear part of the window casing/frame, valance, or sill.

Further, optionally one or more sensors and/or output devices may be modular in nature. For example, a given sensor or output device may be coupled to the window system sill, valance panel, casing (on an interior or exterior side), or other portion via magnets, clamps, screws, or otherwise. By way of illustration, a mounting magnet may be included in a sensor device or output device (e.g., on or proximate to a mounting surface of the device). The mounting magnet may be configured to be magnetically attached to a ferrous material included in the window system (e.g., in the window casing, valence, or sill), thereby maintaining the integrity of the window casing and not requiring unsightly mounting hardware.

Optionally, if a module device is mounted using a screw of bolt, the modular device may be easily added (or removed) by an end user (e.g., a home owner) using readily available simple tools, such as a screw driver or a coin, or simply using fingers.

Optionally, such modular devices may communicate with the window system via a wireless interface, via electrical contacts, via a plug, optically (e.g., via pulsed infrared light emitted using an LED), and/or otherwise.

Optionally, the window system may power a given modular device via induction, via electrical contents, via a plug, and/or otherwise. Optionally, a given modular device may be powered via a separate connection to a power source and/or via a battery (which may or may not be rechargeable). Optionally, some or all of the window system components and modules, may be powered via solar arrays (e.g., of one or more photovoltaic cells).

Optionally, an interface may be provided via which a user may manually instruct the system to perform various actions (e.g., open/close windows, shades, blinds, locks; change window color/shade, change thermostat settings, capture images, monitor a pet, turn on a light, activate an alarm, turn on/off a fireplace, turn on/off an appliance, etc.) via an application installed on a user device, via a browser-based user interface, via physical switches/controls, via a microphone, via a camera, or otherwise. In addition or instead, one or more algorithms may utilize and control the various devices and reporting mechanisms described herein based on sensor inputs, calendar/clock data, data received from other systems, user settings, and/or user or manufacturer rules. Optionally, a user interface may be provided via which a user may schedule certain actions to occur by day and/or time (e.g., opening or closing windows, locking or unlocking windows and doors, open or closing shades, changing a window transmissivity, changing a window color, adjusting thermostats, turning appliances on or off, arming or disarming an alarm system, other actions disclosed herein, or the like).

Thus, for illustrative example, the window system may utilize sensor inputs (e.g., rain sensor, barometer, humidity, temperature, and/or other sensor inputs) to detect rain or a likelihood of rain, and close windows and/or transmit notifications to a user device in response. By way of further example, the window system may utilize sensor inputs (e.g., glass breakage sensor (e.g., a vibration and/or sound detection sensor), window position sensor, microphone, camera, motion sensor, and/or proximity sensor inputs) to detect an unauthorized entry or entry attempt, and cause an audible alarm via a speaker, turn on lights, flash lights, change the color of exterior and/or interior lights (e.g., to red), generate light patterns, change intensity of lights (e.g., brighten or dim), point lights, close windows, close shades, close blinds, close doors, lock windows, lock doors, call one or more emergency numbers, record images of the intruder/house/grounds using cameras, point cameras, stream camera images to specified destinations, transmit short message notifications to one or more user-specified destinations (e.g., including text identifying the attempted break-in and including related images or links to related images), and/or perform other tasks.

By way of still yet further example, the window system may utilize sensor inputs (e.g., from a medical alert device (e.g., a wearable device worn by a user), microphone, and/or camera) to determine that a person within the building may be undergoing a medical emergency (e.g., a heart attack, a hypoglycemia episode, an accident, etc.). In response to such detection, the window system may call one or more pre-specified emergency numbers, capture and transmit images of the person (using a camera and network interface) to pre-specified destinations, capture and transmit voice communications from the person (using a microphone and network interface) to pre-specified destinations, transmit short message notifications to one or more user-specified destinations (e.g., including text identifying the medical emergency and including related images or links to related images), turn on lights, flash lights (e.g., to attract attention and identify the building to emergency responders), change the color of one or more exterior and/or interior lights (e.g., to red), change the color/shade/transmissivity of one or more windows (e.g., to indicate which window is proximate to the person undergoing the medical emergency), unlock one or more doors to permit emergency responders to enter the building, and/or the like.

By way of yet further example, the window system may utilize sensor inputs (e.g., a GPS system located in a user vehicle or phone that provides current location information) to determine that a user is likely coming home (e.g., via a message from the GPS system or user phone that indicates that the user has asked to be navigated home, or by monitoring the route the user is following). The window system may estimate at what time the user will arrive home based on the current distance from the home and real time traffic information. The estimated time may be provided via a third party system accessed by the window system over a network. The window system may also determine the current temperature of the house via a temperature sensor. The window may determine whether it is daylight (e.g., via a calendar and clock and/or via a light sensor). Based on the current time, the time it will take for the user to arrive home, and whether it is daylight or not, the window system may decide whether and when to change a thermostat setting (e.g., to turn on a heater or air conditioner and set it to a specified temperature), whether and when to open or close window shades, and/or whether and which interior/exterior lights to turn on. If the system determines that the user is at an exterior door, the window system may unlock the door to permit entry.

One or more user interfaces may be provided that reports on the determined status of the window system and connected components, as well as sensor readings. For example, a user interface may indicate the interior and/or exterior temperature at each window, current window light transmissivity, window open/close indications, lights on/off indications, and/or other status information. User interfaces may also enable the user to select images or video streams from one or more cameras connected to the window system.

Certain example aspects will now be described with respect to the figures.

FIG. 1 illustrates an example architecture, including sensors 104 (which may include analog to digital convertors to convert analog sensor readings into the digital domain), one or more smart windows 102, controlled devices (e.g., motors, locks, cameras, sprinklers, shades, irrigation systems, lights, alarms, etc.) 106, a backend system 106, and user terminals 110. Optionally, communications between the smart windows and some or all of the other components may be encrypted using reciprocal encryption or non-reciprocal encryption (e.g., where data may be encrypted using a private key for transmission and decoded using a public key).

One or more windows 102 may be equipped with respective window computer systems. A given window computer system may be configured to control various aspects of the window via corresponding mechanisms, such as opening/closing the window, open/closing window shades, changing the color or transmissivity of the window, controlling lights integral to the window, control user interfaces, and/or other aspects disclosed herein. The window computer may also be configured to control non-integral devices such as those discussed elsewhere herein (e.g., thermostats (e.g., change a temperature setting, change from air conditioning mode to heating mode, change from heating mode to air conditioning mode, turn on fan without heat or air conditioning, etc.), lights (turn on/off, change lighting intensity, change lighting color, etc.), appliances, irrigation valves, the locks/blinds/cranks of other windows or doors, alarms, etc.), via wired and/or wireless networks (e.g., Ethernet, WiFi, Bluetooth, ZigBee, cellular, etc.).

The window computer system may also be configured to receive sensor data from sensors 104. Some sensors may optionally be integral to the window, such as sunlight intensity sensors, barometer pressure sensors, glass flex sensors, rain sensors, interior/exterior temperature sensors, air quality sensors, pollen sensors, cameras, glass break sensors, microphones, and/or other sensors discussed herein. The window computer may also be configured to receive data from non-integral sensors, such as those discussed elsewhere herein, via wired and/or wireless networks (e.g., Ethernet, WiFi, Bluetooth, ZigBee, cellular, etc.). For example, the window computer system may be configured to receive sensor data from remote cameras, temperature sensors, rain sensors, user interfaces, microphones, alarm sensors, GPS radios, medical sensors, breakage sensors, light sensors, proximity sensors, and/or the like.

The window system may be configured to interact with output devices 106, such as thermostats, AC outlets, appliances, irrigation valves, sprinkler systems, pumps, lights, light positioning motors, camera positioning motors, mechanisms of other windows, door mechanisms, speakers, user interface devices, and/or other devices discussed herein.

Not all of the windows need include the window computer system discussed above. For example, some windows may have low-cost IoT devices with low power microcontrollers and limited memory, sufficient to receive and execute commands, and may not have direct access to remote sensors.

The window system may receive user instructions and settings from one or more terminals 110 (e.g., a smart phone, a tablet, a laptop, a desktop computer, a networked wearable device (e.g., a smart watch), a networked smart speaker configured to receive voice commands, a networked appliance, a vehicle system, etc.) and may provide sensor readings, notifications, user interfaces, and/or other data to the terminals 110. The window system may communicate with the terminals 110 directly (e.g., via direct WiFi, Bluetooth, etc.), via a local WiFi router, or remotely via the Internet or other network. Thus, a user may be able to control the window systems 102 remotely, and be able to receive sensor readings remotely. The window systems 102 may communicate with a remote backend system (e.g., a cloud-based system) to provide sensor data, receive software updates, receive commands, receive device configuration information, receive data (e.g., weather, traffic, etc.), and/or the like.

Figure 2:
FIG. 2 illustrates an example software stack.

FIG. 2 illustrates an example software stack that may optionally be used in conjunction with the architecture described herein. Not all the layers need be present. Advantageously, the software stack enables existing or new sensors and output devices to be easily added to the system. Layer 202 constitutes the edge layer comprising sensors, motorized devices, and other devices. Portions of the edge layer may be integrated into one or more windows. The sensors collect data and provide the data via wired and/or wireless networks. The motorized devices may be controlled via a wired or wireless network as described herein.

Layer 204 converts sensor data into a target format using one or more protocols. Layer 204 may also determine if certain sensor data meet respective thresholds (e.g., to ensure the sensor data is not just noise). Layer 206 is a connectivity layer provides wired and/or wireless connectivity to the edge devices. Layer data abstraction layer 208 may facilitate interoperability and platform independence and may optionally act as a security layer. Layer 210 may act as an aggregation layer. Product and business logic may be implemented at this layer.

Layer 212 is a presentation layer and/or decision taken layer. This layer may be utilized to apply machine learning and/or custom logic to generate decisions and to control devices at the edge layer 202. Layer 214 acts as a user interface layer via which users may interact with systems and devices.

Figure 3:
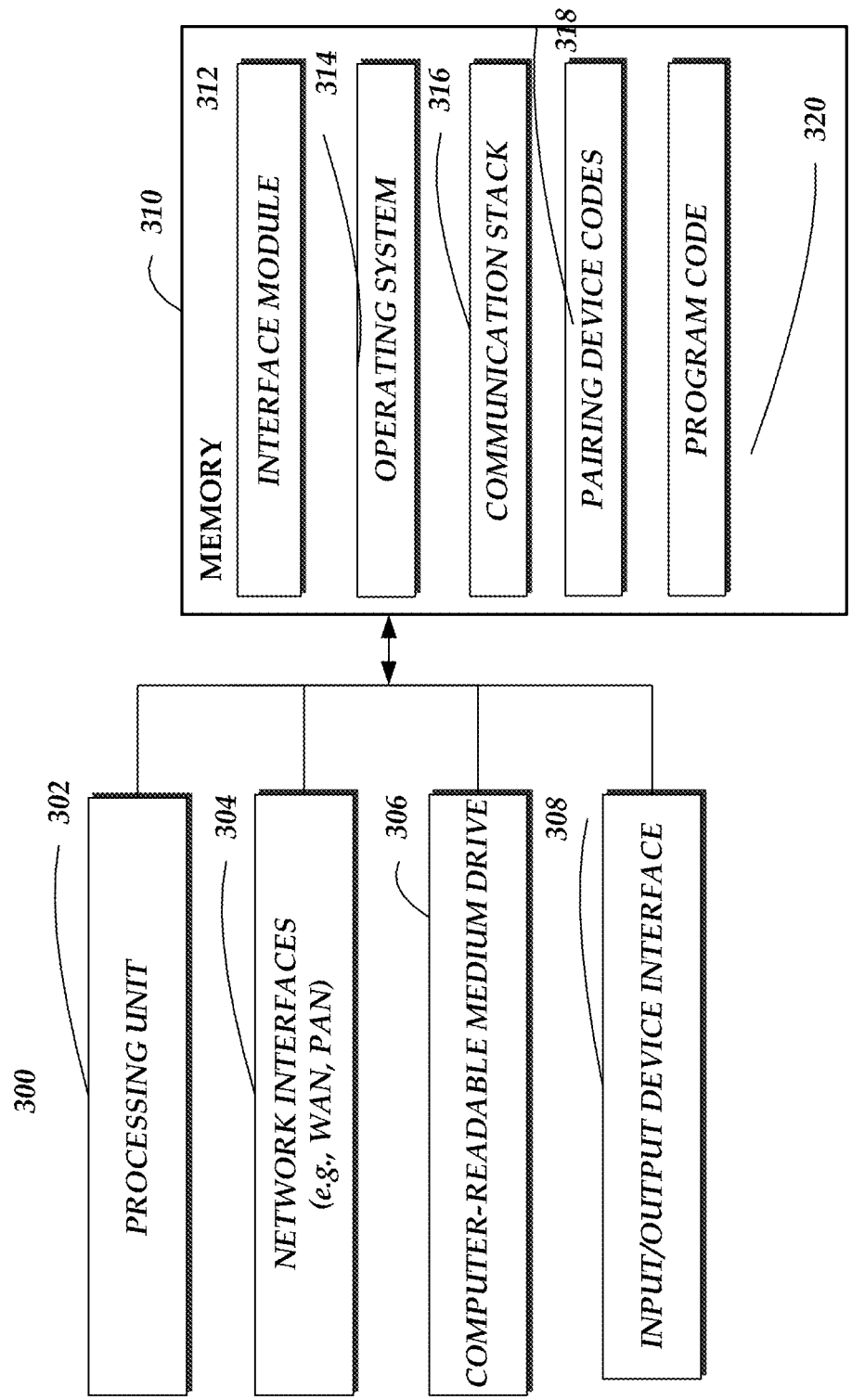
FIG. 3 is a block diagram illustrating example components of a window computer system.

FIG. 3 is a block diagram illustrating example components of a window computer system 300. The example window computer system 300 includes an arrangement of computer hardware and software components that may be used to implement aspects of the present disclosure. Those skilled in the art will appreciate that the example components may include more (or fewer) components than those depicted in FIG. 3.

The window computer system 300 may include one or more processing units 302 (e.g., a general purpose processor, an encryption processor, a video transcoder, a high speed graphics processor, and/or a microcontroller (e.g., with an integral or external analog-to-digital converter to convert analog sensor signals to the digital domain and/or a digital to analog converted to convert digital data to the analog domain to control device with analog inputs), one or more network interfaces 304 (e.g., WiFi, Bluetooth, ZigBee, cellular, NFC interfaces), a non-transitory computer-readable medium drive 306, and an input/output device interface 308, all of which may communicate with one another by way of one or more communication buses. The network interfaces 304 may be coupled to corresponding antennas.

The processing unit 302 may thus receive information and instructions from other computing devices, systems, or services via a network. The processing unit 302 may also communicate to and from memory 306 and further provide output information via the input/output device interface 308. The input/output device interface 308 may also accept input from various input devices, such as sensors (e.g., sensors 104), a keyboard, mouse, digital pen, touch screen, microphone, camera, etc.

The memory 310 may contain computer program instructions that the processing unit 302 may execute in order to implement one or more embodiments of the present disclosure. The memory 302 generally includes RAM, ROM and/or other persistent or non-transitory computer-readable storage media. The memory 302 may store an operating system 314 that provides computer program instructions for use by the processing unit 302 in the general administration and operation of the communication stack 316, device codes 318, and program code 320. The memory 310 may further include other information for implementing aspects of the present disclosure. For example, the memory may stores encryption and decryption keys to decrypt data be transmitted by the computer system 300 and to decrypt data received by the system 300.

The communication protocol stack 316 may include stacks for each of the network interfaces (e.g., for the WiFi, Bluetooth, ZigBee, and/or cellular interfaces). The pairing device codes 318 may store a unique codes received from devices during a pairing process.

In the illustrated example, the memory 310 includes an interface module 312. The interface module 312 can be configured to facilitate generating one or more interfaces through which a compatible computing device, may send to, or receive from, the communication protocol stack 316, device codes 318, and program code 320.

The modules or components described above may also include additional modules or may be implemented by computing devices that may not be depicted in FIG. 3.

Figure 4B:
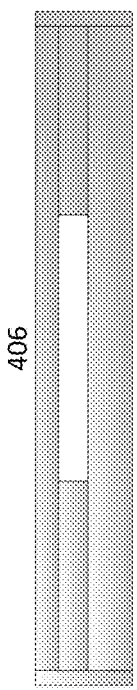
FIGS. 4A, 4B, 4C, and 4D illustrate example aspects of a smart window.
Figure 4A:
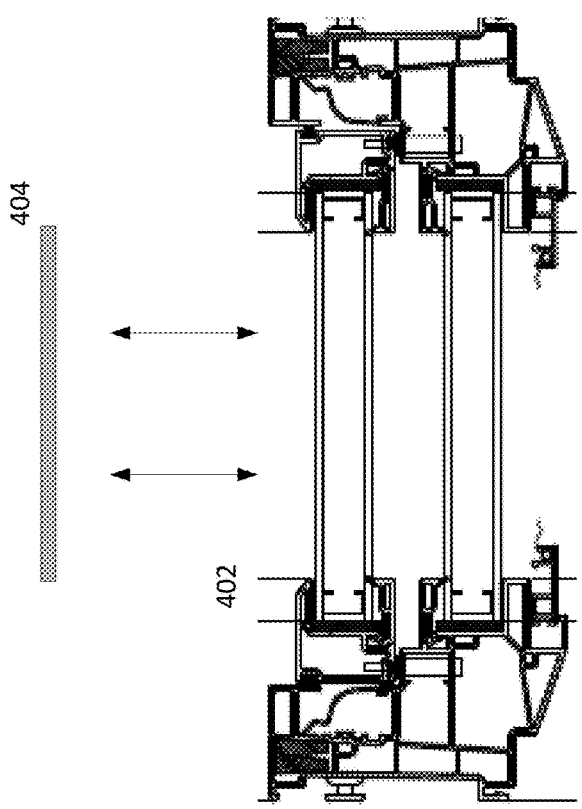
Figure 4C:
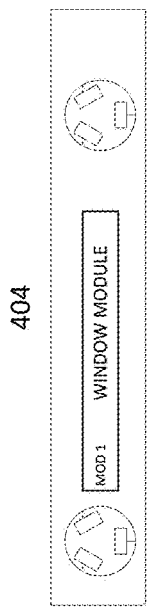

FIGS. 4A, 4B, 4C illustrate example mechanical aspects. FIG. 4C illustrates a front view of an example window (or door) computer system module 404. The module 404 may optionally include one or more connectors to receive power and sensor signals from the window. The connectors may mate with matching connectors in the window (or door). Optionally, power and/or signals may be communicated using other techniques, such as induction. FIG. 4A illustrates a top plan view of the window computer module 404 being inserted into a double hung window casement 402. Of course other window types may be used, such as single hung windows, sliding windows, casement windows, awning windows, bay windows, garden windows, etc.

Rather than being inserted into a window casing as discussed above, the window computer system may optionally be inserted into a receiving area of a window valance, such as valance 406 illustrated in FIG. 4C. The valance may include a rectangular-shaped box or frame, which may be decorated with fabric. The window valance may be used to conceal curtain rods or window blind assemblies. Optionally, a panel may be provided to cover the receiving area and the window computer system 404 when inserted into the valance 406. The module 404 connectors may mate with matching connectors in the valance receiving area to receive power and sensor signals via the valance (which in turn may receive sensors and power from the window). Optionally, the module housing may include one or more circuit card on which the system illustrated in FIG. 3 may be mounted. Optionally, the module 404 may be a single card without its own housing. Optionally, the module 404 may be a single integrated circuit. Optionally, the module 404 may be configured as a processor "stick" with a connector (e.g., a USB A/B/C connector, a Lighting connector, or other standard or non-standard male or female connector) that mates with a mating connector on the window (or door) frame, casing, or valance.

The window or door may be vinyl, aluminum, wood, or some combination of the foregoing. Other materials may be used as well.

Figure 4D:
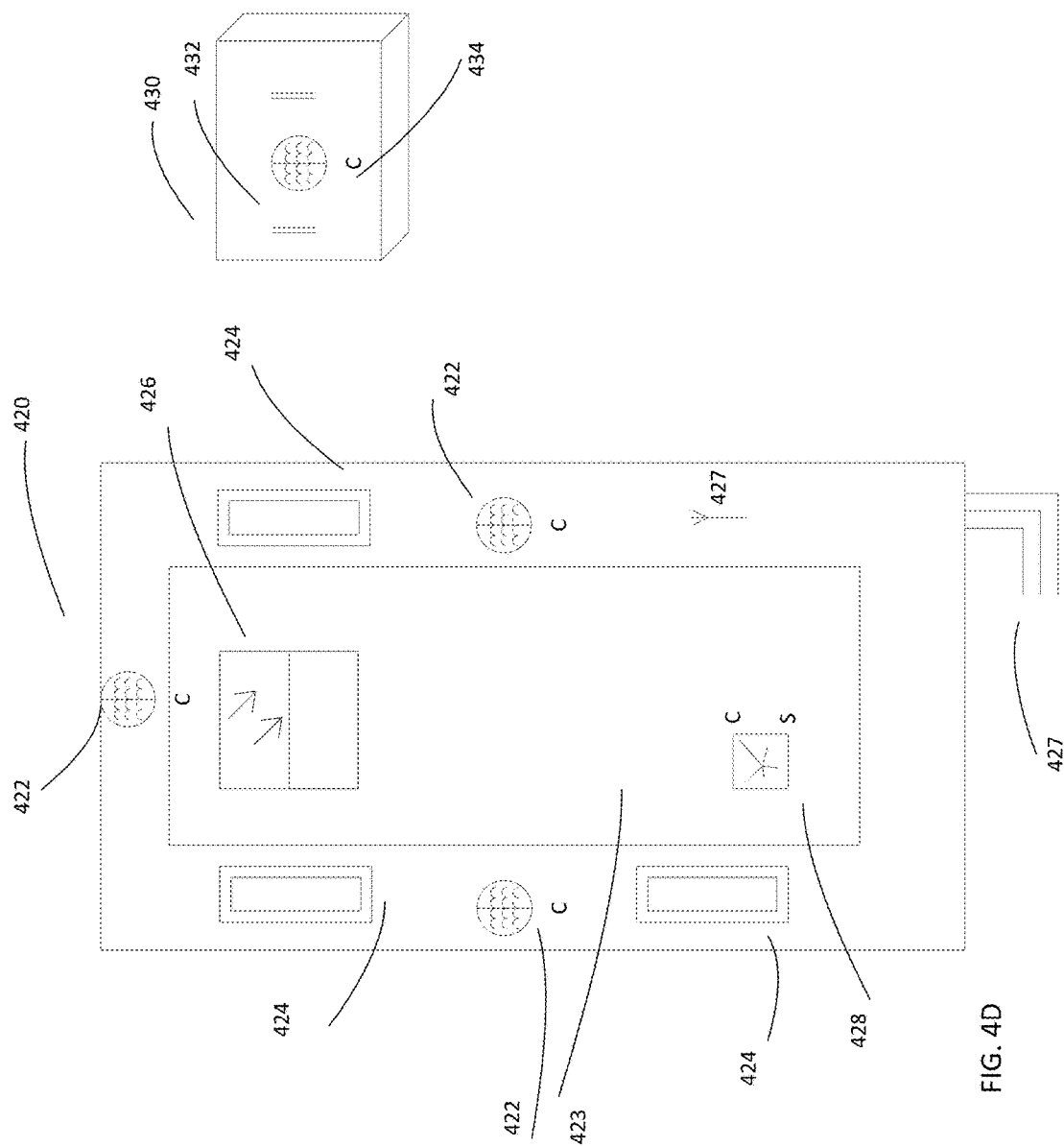

FIG. 4d illustrates an example of a sensor-equipped window 420 and an example of a sensor module 430. Sensors 424 (e.g., temperature sensors, barometric pressure sensors, photoelectric sensors, other sensors disclosed herein, and/or the like) may be embedded in the window or door frame, on the exterior side and/or on the interior side. For example, the sensors may include temperature sensors to sense both internal and external temperature of a building. Portions of the window glass 423 are optionally coated with substantially transparent devices, such as breakage sensors 428, photovoltaic cells 426, photoelectric sensors, flex sensors, rain sensors, and/or the like.

The sensors affixed to the frame may be affixed to recessed portions of the frame configured to receive the sensors. Optionally, the sensors in such recess may be covered by a suitable material, where possible. For example, if a UV light sensor is set in a recess of the frame, a material may be used to cover the sensor that is substantially transparent to UV light. The exterior side of the sensor cover may be of the same color and surface texture as the frame surface so as to blend in and be difficult to see.

A window may include one or more sashes, wherein a given sash may optionally include a left vertical stile, a right vertical stile, an upper horizontal rail, a lower horizontal rail, and one or more panes. Where there is more than one pane, the panes which may be mounted to and separated by muntins/grills. The sashed may be fixed or moveable (e.g., openable in a vertical direction, openable in a horizontal direction, openable by rotating the sash around a hinge point, etc.). A given sash may include a sash pull via which a user may pull the sash open. Where the window is a double or triple pane window, a sensor, where appropriate, may be positioned within the pane stack, rather than on a pane side that can be touched. Thus, for example, a sensor (e.g., a photoelectric sensor, a glass flex sensor, or the like) or photovoltaic cell may be affixed to a pane side that is within the pane stack.

The window 420 may be wired via one or more leads 427 to receive power and/or to communicate with other devices (e.g., the window computer system). The wires 427 may be coupled to wiring run through or on a wall in which the window 420 is mounted. For example, sensor readings from the window sensors and/or commands to the window (e.g., to change the color or shading of the window) and/or devices affixed to the window (e.g., motors, cameras, lights, and/or the like) may be communicated via the leads 427.

One or more induction coils 422 may be embedded in the window frame, sash, or casing The induction coils 422 may be used to wirelessly power modules 430 when affixed over a given indication coil. For example, a module 430 may include one or more permanent magnets 432 to enable the module 430 to be removably affixed to the window 420 (e.g., to a ferrous plate affixed to or embedded within the window frame, sash, or casing), and the module 430 may include one or more inductions coils 434 to wirelessly receive power via the window 420. For example, the module 430 may be a peripheral that includes sensors, lights, motors, network interfaces, and/or the like. The window 420 may further include a ferrous material at one or more locations which act as magnetic mounting locations for modules 430 that having permanent magnets affixed thereto. The window may also include one or more antennas 427 which may be connected to respective wireless network interfaces (e.g., WiFi, Bluetooth, ZigBee, cellular). Certain information may be stored in non-volatile memory internal to or accessible by the window. For example, a window memory device may store the window unit size, model, and features, and may store information regarding the user, such as name or other user identifier, email address, physical address, SMS phone number, name of room the window unit is installed in, and/or other information. This information may be transmitted to a remote system for monitoring or when reporting a failure (e.g., a failure detected by the window or remote system).

Some of the information may optionally have been stored when the window unit was manufactured and prior to shipment to the user, and some of the information (e.g., address, user name, user email, name of room window installed in) may have been stored during or after installation of the window (e.g., during a registration process).

Certain example processes will now be described.

In conjunction with various devices, such as, by way of example, networked doors, indoor room lighting, sprinkler systems, ventilation systems, and/or outdoor lighting, a smart window may optionally communicate with wearable med-alert buttons, such that detection of a press of the alert button (or other such control that indicates an emergency) would cause the smart window to carry out certain tasks. For example, the window, in response to detecting the activation of the alert control, may unlock doors and windows, open doors (e.g., a garage door), turn on room lighting for the room in which the med-alert wearer is located, turn on outdoor sidewalk and/or porch lighting, or the like, in expectation of an emergency crew arrival. This may grant the emergency crew easy access to the home and may inform the emergency crew as to the location within the home of the emergency.

Optionally, in response to a heat or smoke event detected by a heat or smoke detector has alarmed networked to the window, the window may activate a sprinkler system and/or ventilation system (e.g., to exhaust smoke or inject air) for the affected areas. Further, the window may deactivate sources that may worsen emergency condition (e.g., the window may turn close a gas fireplace valve and/or furnace if more than a certain threshold of heat and/or smoke are detected).

By way of further example, in response to detection of a breakage of a window via a breakage detector, the window may transmit a message or signal to the homeowner and/or the window manufacturer's customer service department regarding the breakage. For example, the breakage message may be composed to include data obtained by the window system regarding the address of the home/building where the breakage was detected, an identification of the window unit size, model, and/or features. This information may facilitate the repair or replacement of the window unit by the manufacturer. Optionally, in response to a detected breakage or motion sensor reading that indicates a break-in has or is occurring, the window may take other actions, such as locking some or all networked exterior doors and windows equipped with lock motors, closing and/or locking garage doors, turning on some or all interior and exterior lights, initiating video recording with outdoor surveillance cameras, etc.

By way of further example, if a detector detected a condition that met certain parameters, a window may optionally perform one or more of the following acts:

a. Call, text, email, and/or otherwise communicate with emergency response teams systems, neighbors, relatives, emergency contacts designated by the user, and/or the like, to communicate information related to the emergency (e.g., the cause of the alert (e.g., detected fire, smoke, break-in, etc.), which detectors triggered the alert, the physical address of the structure in which the window is installed, the room(s) where an alert condition was detected, the name of people that are in the vicinity of the alert condition, video, still image, and/or audio information captured using cameras and microphone), and request an emergency response;

b. Generate an audible alarm via speaker and/or siren (where the alarm may include audible words (e.g., pre-stored on the window or generated using a voice synthesis device) that indicate the cause and source of the emergency condition (e.g., "fire detected in kitchen") and/or the audible alarm may be in the form of a loud prolonged sound), change color and/or transmissivity of one or more windows, flash exterior lights and/or change color of exterior lights (e.g., to red) to indicate an emergency and indicate the location in the house of the emergency;

c. Display a text and/or icon message indicating the cause of the alarm and/or the location of the corresponding condition via one or more window displays and/or other displays;

d. Use visible light sensors to detect light levels inside and outside the home, and activate interior or exterior lights to: illuminate the room/area where the emergency condition exists, to illuminate a safe passageway to escape the emergency condition, and/or other illuminate all interior and exterior lights;

f. Evaluate blind/shade status via using information from respective position sensors, and open blinds/shades as desirable via respective shade/blind motors (e.g., to illuminate or grant access to the room/area where the emergency condition exists, to illuminate or grant access to a safe passageway to escape the emergency condition, etc.);

h. Evaluate window lock status for one or more windows using information from respective lock sensors, and unlock windows as desirable via respective lock/unlock motors (e.g., to grant access to the room/area where the emergency condition exists, to grant access to a safe passageway to escape the emergency condition, etc.);

j. Evaluate window open/close status for one or more windows via information from respective position sensors, and open windows as desirable via respective motors (e.g., to grant access to the room/area where the emergency condition exists, to grant access to a safe passageway to escape the emergency condition, etc.);

k. Deploy one or more safety ladders via an auto-deploy safety ladder motor (e.g., to grant access to the room/area where the emergency condition exists, to grant access to a safe passageway to escape the emergency condition, etc.);

l. Turn off furnace and/or gas valve.

By way of yet further example, a window may be used to enhance the comfort, health or convenience of a structure or user. For example, a window may monitor air quality (e.g., continuously or periodically monitor air quality) via one or more sensors (e.g., rain sensors, pollen count sensors, dust sensors, and/or the like), and/or weather conditions via one or more sensors (e.g., rain sensors, outdoor temperature sensors, sunlight intensity sensors, and/or the like). In response to an unfavorable change in home exterior conditions that satisfy certain criteria (e.g., where one or more designated sensors indicate that one or more sensed condition exceed a respective threshold), the window may perform one or more of the following acts:

a. Display a message indicating the current exterior conditions via one or more displays;

b. Communicate with a networked thermostat system to determine desired in-home temperature condition (e.g., by reading a user temperature setting, and/or a user mode setting (e.g., air conditioning, heating, fan);

c. Evaluate whether interior home comfort would better be achieved/maintained by opening or closing one or more windows;

d. Evaluate whether interior home comfort would better be achieved/maintained by making one or more windows more transparent or less transparent;

e. Detect window lock/unlock and/or window open/closed status via respective sensors;

f. Set electrochromic active panel to the appropriate shade value in accordance with evaluation(s);

g. Unlock or lock windows via respective window lock motors in accordance with evaluation(s); and/or h. Open or close windows via respective window motors in accordance with evaluation(s).

Optionally, a given window may interface with and communicate over a network with remote weather service systems, alert systems, and/or local sensors to automatically determine and respond to expected changes in weather (as determined using information from the weather service system, alert system, and/or local sensors), such as rain, snow, hail, or tornado, by preemptively closing windows, doors, and garage doors using respective motors, and shutting power off to (or turning off) designated non-critical networked outlets, lights, and/or other devices.

Further, the window may be utilized to enable a user to remotely control the window and/or devices connected to the window (e.g., using an application downloaded to a user device, using a web-based service accessed via a browser, using a dedicated remote control device, using a networked microphone/speaker device, using a camera, and/or otherwise). For example, a visual user interface, speech input user interface, and/or camera may be provided that enables a user to command or obtain the status of some or all of the following:

Lock sensor status;
Position sensor status (window or door open/closed);
Position sensor blind status (blind up/down);
Camera(s) (command camera to start recording, stop recording, stream video);
Window lock/unlock motor(s) (command windows to lock or unlock);
Window motor(s) (command windows to open or close);
Shade/blind motor (command shades to open or close); and/or
Window transmissivity (command window to increase or decrease window transmissivity).
Thus, for example, a window may perform some or all of the following acts:

a. Continuously or periodically monitor and window lock status (locked or unlocked), window position status (open or closed, percentage open or closed, etc.), and/or blind position status (up or down, percentage up or down, open or closed, percentage open or closed, etc.), and report such status to a local or remote user device;

b. Carry out instructions (such as those discussed herein) from a user received via a local or remote user device; and/or c. Receive, detect, and carry out instructions (such as those discussed herein) from a user standing before the window camera (or other networked camera) giving commands in the form of gestures via camera.

Figure 5:
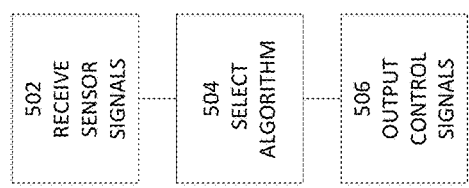
FIGS. 5, 6, 7, 8, and 9 illustrate example processes.

With reference to FIG. 5, an example process is illustrated that may be executed using a smart window equipped with a window computer system. The process may generally be used to process sensor readings and to control devices based at least in part on the sensor readings. More targeted examples are described elsewhere herein. At block 502, sensor readings are received. In addition, data from remote systems may be received (e.g., weather data, traffic data, vehicle location data, user location data, etc.). At block 504, based on an initial analysis of the data received at block 502, an algorithm may be selected. For example, if a barometric pressure drop exceeds a specified threshold, the process may select a rain projection algorithm. At block 506, the process uses the output of the algorithm to control one or more devices, such as one or more of the devices disclosed herein.

Figure 6:
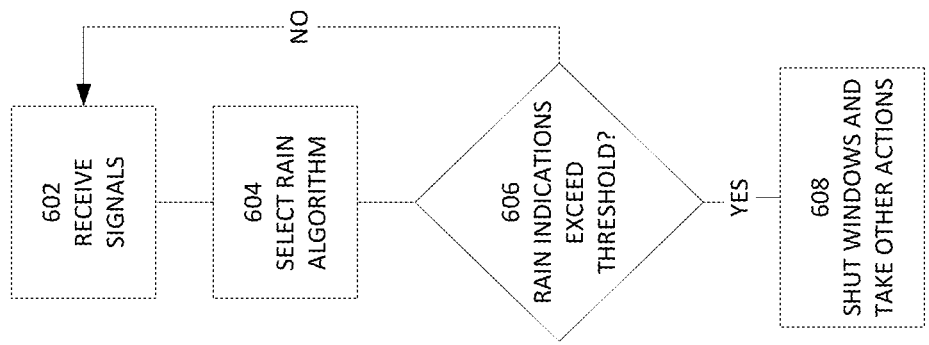

Referring now to FIG. 6, another example is illustrated. In this example, the process determines that a rain management algorithm is to be used in determining how devices are to be controlled.

At block 602, sensor readings and/or information from remote sources are received. For example, the window system sensors may monitor the immediate weather environment, such as humidity, rain, pressure changes, lightning, sunlight intensity, and/or the like using respective sensors. In addition, weather information may be received from a remote weather data system that reports weather information that may not be as local as that reported by the window system sensors. For example, the remote weather data system may report weather on a country, state, city, and/or zip code basis. As described elsewhere herein, the sensor information may also include non-weather-related information, such as information on whether someone is breaking into a building via a window (e.g., via a window position sensor (e.g., a magnetic sensor that detects an opening of a window by disruption of a magnetic linkage between sensor components) that indicates the window is being opened).

At block 604, the window system may analyze the sensor information and determine if a given algorithm is to be utilized. Readings from different sensors may be assigned different weights (reflecting their importance in determining the algorithm relevancy). Sensor readings may be optionally normalized.

For example, the process may use a formula such as that provided below, to determine whether a given algorithm is to be selected:

$$\text{Relevancy value} = w_1 n_1 S_{reading1} + w_2 n_2 S_{reading1} + \ldots w_n n_n S_{readingn} + w_{1ex} n_{1ex} \text{External}_1 + w_{2ex} n_{2ex} \text{External}_1 + \ldots w_{nex} n_{nex} \text{External}_{nex}$$

Select Algorithm if Relevancy value≥Algorithm threshold
Where:
w=weight
n=normalization factor
$S_{reading\#}$=reading of sensor #
$w_{ex}$=weight for external data
$n_{ex}$=normalization factor for external data
External=external data Rather than using just one reading per sensor, the formula may utilize multiple readings from a given sensor. For example, a certain number of readings from a given sensor may be averaged, and the averaged value may be utilized in the above formula. Other central tendencies (rather than the average value) may be used.

Multiple formulae may be evaluated in parallel or sequentially. A given algorithm formula may use different sensors and/or external data items. For example, a rain management selection algorithm may optionally utilize weather-related sensor readings and not certain security sensor readings (e.g., proximity sensor readings). By contrast, a security management selection algorithm may utilize security-related sensor readings (e.g., breakage sensors, window position sensors, proximity sensors, cameras, microphones, and/or the like) and not certain weather-related sensor readings or weather information from remote systems.

In this example, a rain management algorithm is selected. At block 606, a determination is made as to whether the rain-related sensor readings and/or data from remote systems exceed a rain threshold, wherein the rain threshold indicates the presence and/or likelihood of rain. If the threshold is exceeded, then at block 608, rain management actions are taken, such as closing of motorized windows, skylights, and doors, the turning off of a sprinkler system, the turning on of a dehumidifier, the transmission of alerts, turning on interior and/or exterior lights, and/or the like.

Optionally, a user interface is provided via which the user can specify what actions are to be taken by the system in the event rain or other weather conditions are detected or projected. For example, a user may configure the window system to generate alerts to be transmitted to the user and/or other destinations if certain weather conditions are detected or inferred. By way of illustration, such thresholds may be set by the user using an interface provided via a window system display, via a window system microphone, using a dedicated application (an "app") installed on a user device (e.g., a user phone, tablet, or general purpose computer system), via web service accessed via a browser, or otherwise.

The threshold may relate to specific sensor readings, such as if more than a certain amount of water is detected, if the temperature exceeds or falls below a specified temperature, if the humidity is above or below a threshold level, if more than a certain number of lighting events are detected (e.g., using a camera, or a vibration or sound sensor that detects thunder), or the like. The threshold may also be set for a determined likelihood of a weather event to occur in the near future. For example, the window system (directly or using the computing resource of a remote system) may analyze changes in pressure and humidity and infer whether it is like or unlikely that rain will begin in the vicinity of the window system within a certain period of time (e.g., within the next 30 minutes, the next 60 minutes, the next 2 hours, etc.). The user may specify that if the window system determines that rain is likely within a specified time period it should transmit a notification to the user and/or other destinations. The notifications may be provided via a dedicated application installed on a user device and/or via other communication mediums specified by the user (e.g., via a short messaging service, an email, a voice call, an app alert, or otherwise).

In addition to or instead of a notification, the window system may take other actions specified by the user. For example, if one or more thresholds are satisfied (e.g., humidity, temperature, pressure change, rain, thunder, and/or the like), the user may specify that the window system is to command a window, door, and/or skylight motor to close or open, that a dehumidifier be turned on or off, that a sprinkler is to be turned off or on, that one or more lights are to be turned on or off, and/or the like.

Figure 7:
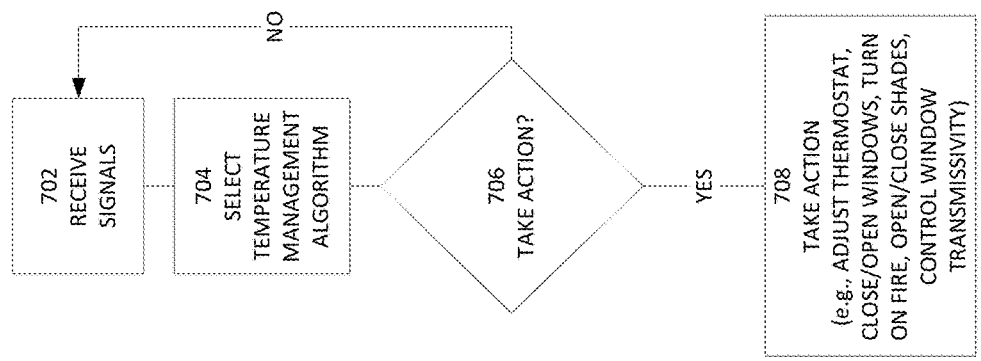

Referring now to FIG. 7, another example is illustrated. In this example, the process determines that a temperature management algorithm is to be used in determining how devices are to be controlled. It is understood that the processes illustrated in FIGS. 6 and 7 (and/or other processes) may be run in parallel.

At block 702, sensor readings and/or information from remote sources are received. For example, the window system sensors may monitor the immediate weather environment, such as internal temperature, external temperature, humidity, sunlight intensity, time of day, calendar date, and/or the like using respective sensors. In addition, weather information may be received from a remote weather data system that reports weather information that may not be as local as that reported by the window system sensors. For example, the remote weather data system may report weather on a country, state, city, and/or zip code basis.

At block 704, the window system may analyze the sensor information and determine which algorithm is to be selected. For example, the process may use a formula such as that discussed above, to determine whether a given algorithm is to be selected.

In this example, a temperature management algorithm is selected. At block 706, a determination is made as to whether the temperature-related sensor readings and/or data from remote systems indicate that certain actions are to be taken (e.g., turn heater on or off, turn air conditioner on or off, turn fan or off, adjust thermostat up or down, turn fireplace on or off, open or close shades, increase or decrease glass light transmissivity, and/or like). As similarly discussed above, a user may specify via one or more user interfaces what actions are to be taken in response to certain sensor readings or temperature projections. Such user specifications may be utilized in determining what actions are to be taken.

At block 708, the actions determined at block 706 are taken.

Figure 8:
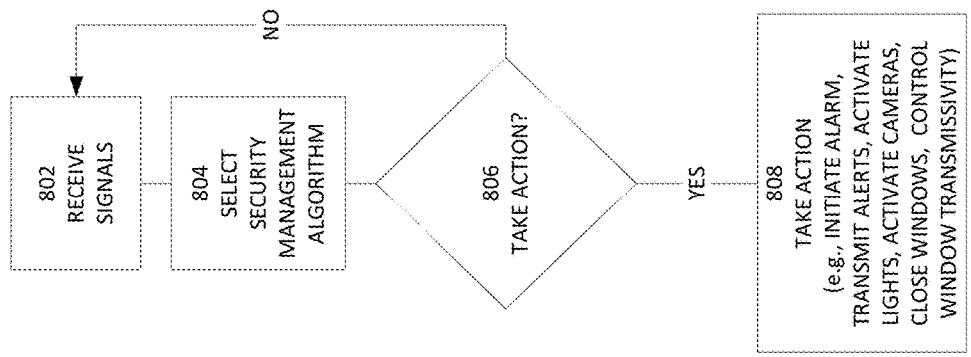

Referring now to FIG. 8, another example is illustrated. In this example, the process determines that a security management algorithm is to be used in determining how devices are to be controlled. It is understood that the processes illustrated in FIGS. 6, 7, and/or 8 (and/or other processes) may be run in parallel.

At block 802, sensor readings and/or information from remote sources are received. For example, the window system sensors may monitor the immediate security environment, such as glass breakage events, change in window position, human proximity, motion, sound, and/or the like using respective sensors (e.g., breakage sensors, window position sensors, proximity sensors, motion sensors, microphones, cameras, or the like).

At block 804, the window system may analyze the sensor information and determine which algorithm is to be selected. For example, the process may use a formula such as that discussed above, to determine whether a given algorithm is to be selected.

In this example, a security management algorithm is selected. At block 806, a determination is made as to whether the security-related sensor readings indicate that certain actions are to be taken (e.g., initiate sounding of alarm, transmit alerts (e.g., app alerts, text messages, voice calls, and/or the like to destinations specified by the user, to police or other security services), turn on lights, flash lights, change the color of lights (e.g., to red), position/rotate lights to point at a detected break in, activate cameras, position/rotate cameras to point at a detected break in, close windows, close doors, control window transmissivity, and/or like). As similarly discussed above, a user may specify via one or more user interfaces what actions are to be taken in response to certain sensor readings or determined security incidents. Such user specifications may be utilized in determining what actions are to be taken.

At block 808, the actions determined at block 806 are taken.

Figure 9:
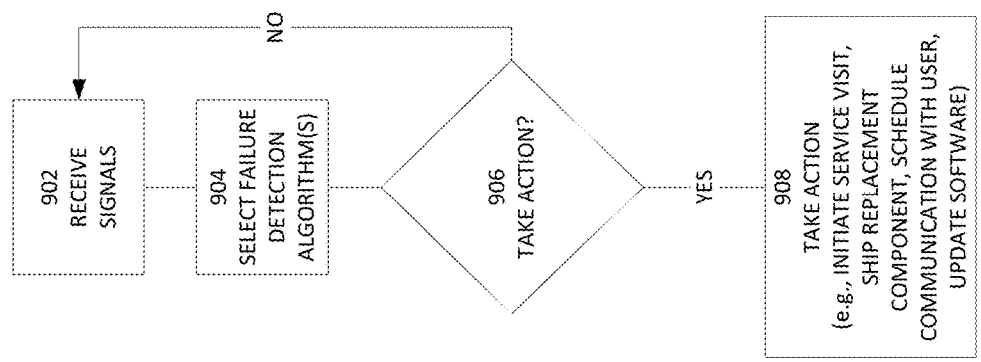

Referring now to FIG. 9, an example fault management process is illustrated. The fault management process may be utilized to detect faults in one or more smart windows or devices interfaced thereto (e.g., sensors, output devices, user interfaces, etc.). This process may be periodically executed and/or may be executed in response to one or more fault indications. The process may be partially executed by one or more window systems and partially by a backend system.

At block 902, sensor readings and/or fault notifications are received. For example, a pressure sensor between two panes in a double or triple paned window may report on the pressure between the two panes, where the gap between the two panes is supposed to contain a noble gas, such as argon or krypton gas. By way of further example, a glass breakage sensor may indicate the presence of a cracked or broken pane. By way of yet further example, a window computer system may perform its own self check and report any failures (e.g., memory failures, input/output device failures, modem failures, etc.). Optionally, the sensor readings and/or fault notifications are transmitted to a backend system for evaluation.

At block 904, one or more failure detection and evaluation algorithms may be selected (e.g., by the backend system or the window computer system). For example, if a pressure sensor indicates that a measured pressure has dropped a certain amount or is below a specified threshold, then a pressure failure algorithm may be selected. The pressure failure algorithm may utilize one or more pressure sensor readings, temperature sensor readings, altitude information, barometric pressure sensor readings, and/or the like in determining whether a leak of the gas between the panes is or has occurred. By way of further example, if a memory fault indication is received, then a window computer system failure algorithm may be selected. By way of yet further example, if a sensor reading is determined to be outside of an upper or lower threshold (indicating an invalid reading), a corresponding sensor failure algorithm may be selected.

At block 906, a determination is made by the selected algorithm(s) as to what action to take. For example, if there is a failure detection of the window computer system, the process may instruct the window computer system to reboot, may download new code to the window computer system, or take other remediation acts. If the window computer system still has a failure, it may be determined that a service visit should be initiated to the window location to test and/or repair the window computer system. By way of further example, if window computer system has a failure it may be determined that a replacement component is to be shipped to the user of the window computer system for installation to replace the corresponding failed component.

By way of yet further example, if there is a pressure failure detected, the process may determine that a service visit should be initiated to the window location to test and/or repair or replace the window. At block 908, the determined action is taken (e.g., initiate a service visit, initiate a call with user, ship replacement component, reboot system, update software, etc.). Optionally, the window transmits, during the process, information regarding the window (e.g., unit size, model, features, and/or a name of room the window unit is installed in), and/or information regarding the user (e.g., name or other identifier), email address, physical address, SMS phone number, and/or other information) to the backend system.

It is understood, that while certain aspects of the disclosure are discussed with respect to windows, these aspects may be utilized with other objects, such as doors. For example, certain modular systems may be configured to be inserted into or otherwise attached to a door frame or door.

Thus, example systems and methods are disclosed that utilize a smart window that includes sensors, output devices, and/or a local processing device to provide a variety of services.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "may," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

While the phrase "click" may be used with respect to a user selecting a control, menu selection, or the like, other user inputs may be used, such as voice commands (received via a microphone), text entry (e.g., received via a keypad or touch screen), gestures (e.g., received via a touch screen or via a camera viewing the gestures), etc. User inputs (e.g., instructions) may, by way of example, be provided via an interface, such as via text fields, wherein a user enters text, and/or via a menu selection (e.g., a drop down menu, a list or other arrangement via which the user can check via a check box or otherwise make a selection or selections, a group of individually selectable icons, etc.), via voice (using a microphone), via a gesture (using a camera or touch screen), via a facial expression (using a camera), and/or otherwise. When the user provides an input or activates a control, a corresponding computing system may perform the corresponding operation. Some or all of the data, inputs and instructions provided by a user may optionally be stored in a system data store (e.g., a database), from which the system may access and retrieve such data, inputs, and instructions. The notifications and user interfaces described herein may be provided via a Web page, a dedicated or non-dedicated phone application, computer application, a short messaging service message (e.g., SMS, MMS, etc.), instant messaging, email, push notification, audibly, and/or otherwise.

The user terminals described herein may be in the form of a mobile communication device (e.g., a cell phone), laptop, tablet computer, interactive television, game console, media streaming device, head-wearable display, networked watch, etc. The user terminals may optionally include displays, user input devices (e.g., touchscreen, keyboard, mouse, voice recognition, etc.), network interfaces, etc. While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

What is claimed is:

1. An openable barrier unit comprising a window, a door, or a skylight, comprising:
    a frame;
    a glass pane;
    a wireless network interface;
    a receiving area configured to removably receive a removable openable barrier unit computer system, the receiving area comprising a first connector, the first connector configured to couple with a second connector of the removable openable barrier unit computer system and to provide power to the removable openable barrier unit computer system;
    the removable openable barrier unit computer system,
    the removable openable barrier unit computer system comprising:
        a housing;
        the second connector configured to couple with the first connector;
        non-volatile memory configured to store openable barrier unit model information;
        a processing device located within the housing;
        non-transitory memory located within the housing configured to store instructions to be executed by the processing device,
        wherein the instructions, when executed by the processing device, enable the openable barrier unit to:
        communicate using the wireless network interface with other openable barrier units as a node in a mesh network;
        access a decryption key;
        decrypt, using the accessed decryption key, encrypted data received by the openable barrier unit;
        utilize weights and normalization factors for sensor readings for each sensor in determining what action to take;
    transmit a model information of the openable barrier unit accessed from the non-volatile memory of the removable openable barrier unit computer system to a remote destination in response to a first event; and
    a plurality of sensors of different types affixed to the openable barrier unit and coupled to the openable barrier unit computer system, including at least one of;
    a breakage sensor,
    a proximity sensor,
    a sound sensor,
    a vibration sensor,
    a temperature sensor,
    a humidity sensor,
    a light intensity sensor,
    a barometric pressure sensor,
    a moisture sensor,
    a smoke sensor, or
    a carbon monoxide sensor;
    wherein the openable barrier unit computer system is configured to take at least a first action in response to at least a first weighted and normalized sensor reading from a first sensor of the plurality of sensors, the first action comprising:
    controlling a motor coupled to a lock of a different openable barrier unit.

2. The openable barrier unit as defined in claim 1, further comprising:
    a sash a sash sensor configured to detect a position of the sash, the sash sensor coupled to the openable barrier unit computer system;

a magnet or ferrous material comprised by the frame or the sash configured to magnetically couple a module to the openable barrier unit; and an interface configured to receive and/or transmit signals to one or more devices included in the module.

3. The openable barrier unit as defined in claim 1, wherein the wireless network interface comprises at least one of a Ethernet, WiFi, Bluetooth, ZigBee, or cellular wireless network interface.

4. The openable barrier unit as defined in claim 1, further comprising a wired network interface.

5. The openable barrier unit as defined in claim 1, further comprising an AC power supply configured be connected to an AC power source and/or a battery configured to power at least the openable barrier unit computer system and the wireless network interface.

6. The openable barrier unit as defined in claim 1, further comprising:
 a battery; and
 an integral photovoltaic system configured to recharge the battery and/or power at least one sensor.

7. The openable barrier unit as defined in claim 1, further comprising a photovoltaic device substantially transparent to visible light overlaying the glass pane.

8. The openable barrier unit as defined in claim 1, further comprising:
 a sash;
 a sash sensor coupled to the openable barrier unit computer system, the sash sensor configured to detect at least:
  an open position of the sash;
  a closed position of the sash; and
  an intermediate position of the sash, the intermediate position between the open position and the closed position.

9. The openable barrier unit as defined in claim 1, further comprising:
 a sash; and
 a sash sensor configured to detect a position of the sash, the sash sensor coupled to the openable barrier unit computer system.

10. The openable barrier unit as defined in claim 1, wherein the plurality of sensors of different types comprises at least one sensor wirelessly coupled to the openable barrier unit computer system.

11. The openable barrier unit as defined in claim 1, wherein the plurality of sensors of different types comprises at least one lock sensor configured to detect a lock position.

12. The openable barrier unit as defined in claim 1, wherein the plurality of sensors of different types comprises a motion sensor and a rain sensor.

13. The openable barrier unit as defined in claim 1, wherein a second action that the openable barrier unit computer system is configured to take in response to at least a second sensor reading from a second sensor comprises providing a control signal to a shade motor and/or a blind motor.

14. The openable barrier unit as defined in claim 1, wherein the glass pane further comprises an electro-chromatic panel, wherein a second action that the openable barrier unit computer system is configured to take in response to at least a second sensor reading is to change a light transmissivity of the electro-chromatic panel.

15. The openable barrier unit as defined in claim 1, wherein the first action that the openable barrier unit computer system is configured to take in response to at least the first reading from the first sensor comprises:
 turning on a light; and
 transmitting a notification message reporting the first sensor reading to one or more remote devices.

16. The openable barrier unit as defined in claim 1, wherein the plurality of sensors of different types comprises a camera, wherein the first action that the openable barrier unit computer system is configured to take in response to at least the first sensor reading from the first sensor comprises causing the camera to record an image.

17. The openable barrier unit as defined in claim 1:
 further comprising at least one motor coupled to a lock, wherein the first action that the openable barrier unit computer system is configured to take in response to at least the first sensor reading from the first sensor comprises controlling the motor coupled to the lock.

18. The openable barrier unit as defined in claim 1, wherein the first action that the openable barrier unit computer system is configured to take in response to at least the first sensor reading from the first sensor comprises activating a motor affixed to a different openable barrier unit.

19. The openable barrier unit as defined in claim 1, wherein the first action that the openable barrier unit computer system is configured to take in response to at least the first sensor reading from the first sensor comprises activating a motor configured to limit movement of a movable component of a first device.

20. The openable barrier unit as defined in claim 1, further comprising a touch sensitive control.

21. The openable barrier unit as defined in claim 1, wherein in response to a second sensor reading indicating heat or smoke, a second action that the openable barrier unit computer system is configured to take in response to at least the second sensor reading from the second sensor comprises:
 turning on at least one light;
 transmitting a notification message reporting the first sensor reading to one or more remote devices; and
 instructing a first device remote from the openable barrier unit to cease a first operation.

22. The openable barrier unit as defined in claim 1, wherein a second action that the openable barrier unit computer system is configured to take in response to at least a second sensor reading from a second sensor comprises adjusting a setting of a thermostat.

23. A method of operating an openable barrier comprising at least a first pane, the openable barrier comprising a door, a window, or a skylight, the method comprising:
 monitoring, by a computer system included in the openable barrier, signals from a plurality of different types of sensors, including at least two sensor types of the following sensor types:
  a breakage sensor,
  a proximity sensor,
  a sound sensor,
  a vibration sensor,
  a temperature sensor,
  a humidity sensor,
  a light intensity sensor,
  a barometric pressure sensor,
  a moisture sensor,
  a smoke sensor, or
  a carbon monoxide sensor;

communicating data using a wireless network interface with other openable barriers as a node in a mesh network;
accessing a decryption key;
decrypting, using the accessed decryption key, encrypted data received by the openable barrier;
utilizing weights and normalization factors for sensor readings for each sensor in determining what action to take;
transmitting a model, size, and/or feature related information accessed from non-volatile memory of the openable barrier to a remote destination in response to a first event; and
initiating a first action in response to at least a first weighted and normalized sensor reading from a first sensor of the plurality of different types of sensors, the first action comprising: controlling a component of the openable barrier unit.

24. The method of operating an openable barrier as defined in claim 23, wherein the first action that the openable barrier computer system is configured to take in response to at least the first sensor reading from the first sensor comprises providing a control signal to a shade motor and/or a blind motor.

25. The method of operating an openable barrier as defined in claim 23, wherein the pane comprises an electro-chromatic panel, wherein the first action comprising changing a light transmissivity of the an electro-chromatic panel.

26. The method of operating an openable barrier as defined in claim 23, wherein the first action comprises activating a motor associated with a different openable barrier.

27. The method of operating an openable barrier as defined in claim 23, wherein the first action comprises transmitting an instruction to a thermostat or a camera.

28. The method of operating an openable barrier as defined in claim 23, wherein the first action comprises:
turning on, by the computer system included in the openable barrier, at least one light remote from the openable barrier; and
transmitting, by the computer system included in the openable barrier, a notification message reporting the first sensor reading to one or more remote destinations.

29. The method of operating an openable barrier as defined in claim 23, the method further comprising:
monitoring at least one sensor configured to sense a position of a movable portion of the openable barrier;
monitoring weather information; and
at least partly in response to detecting, from position information from the at least one sensor that the movable portion of the openable barrier is in an open position, and on the monitored weather information, commanding an actuator to close the movable portion of the openable barrier.

30. A barrier unit comprising a window, a door, or a skylight, comprising:
a frame;
a glass pane;
a network interface;
a barrier unit computer system, the barrier unit computer system comprising:
a housing;
a processing device located within the housing;
non-transitory memory located within the housing configured to store instructions to be executed by the processing device, wherein the instructions, when executed by the processing device, enable the barrier unit to:
communicate using the network interface with other devices as a node in a mesh network:
access a decryption key;
decrypt, using the accessed decryption key, encrypted data received by the barrier unit;
utilize weights and normalization factors for sensor readings for each sensor in determining what action to take;
transmit a model, size, and/or feature related indicators accessed from non-volatile memory of the barrier unit to a remote destination in response to a first event; and
a plurality of sensors of different types affixed to the barrier unit and coupled to the barrier unit computer system, including at least one of:
a breakage sensor,
a proximity sensor,
a sound sensor,
a vibration sensor,
a temperature sensor,
a humidity sensor,
a light intensity sensor,
a barometric pressure sensor,
a moisture sensor,
a position sensor,
a smoke sensor, or
a carbon monoxide sensor;
wherein the barrier unit computer system is configured to initiate a first action in response to at least a first weighted and normalized sensor reading from a first sensor of the plurality of sensors, the first action comprising: controlling a component of the openable barrier unit.

* * * * *

UNITED STATES PATENT AND TRADEMARK OFFICE
CERTIFICATE OF CORRECTION

PATENT NO. : 10,488,837 B2  
APPLICATION NO. : 16/176588  
DATED : November 26, 2019  
INVENTOR(S) : Christian Aaron Cirino Page 1 of 1

It is certified that error appears in the above-identified patent and that said Letters Patent is hereby corrected as shown below:

On the Title Page

The drawing at the bottom of the page and in the Drawings, In FIG. 1, reference numeral 104, Line 2, delete "PROXIMTY/" and insert -- PROXIMITY/ --.

In the Specification

In Column 5, Line 19, delete "(e.g.," and insert -- e.g., --.

In Column 6, Line 30, delete "network," and insert -- network. --.

In Column 10, Line 39, delete "(e.g.," and insert -- e.g., --.

In Column 12, Line 42, delete "casing The" and insert -- casing. The --.

In Column 14, Line 57, delete "(e.g.," and insert -- e.g., --.

In Column 19, Line 47, delete "information)" and insert -- information --.

In the Claims

In Column 25, Line 28, Claim 25, delete "the an" and insert -- an --.

In Column 26, Line 20, Claim 30, delete "network:" and insert -- network; --.

Signed and Sealed this  
Twenty-fifth Day of February, 2020

Andrei Iancu  
*Director of the United States Patent and Trademark Office*